United States Patent
Sharma

(10) Patent No.: US 11,493,412 B2
(45) Date of Patent: Nov. 8, 2022

(54) METHOD AND KIT FOR EXOSOMES AND ASSOCIATED BIOMACROMOLECULES CAPTURE

(71) Applicant: Aman Sharma, Sri Ganganagar (IN)

(72) Inventor: Aman Sharma, Sri Ganganagar (IN)

(73) Assignee: Aman Sharma, Sri Ganganagar (IN)

( * ) Notice: Subject to any disclaimer, the term of this patent is extended or adjusted under 35 U.S.C. 154(b) by 841 days.

(21) Appl. No.: 16/462,693

(22) PCT Filed: Nov. 23, 2017

(86) PCT No.: PCT/IB2017/057360
§ 371 (c)(1),
(2) Date: May 21, 2019

(87) PCT Pub. No.: WO2018/096481
PCT Pub. Date: May 31, 2018

(65) Prior Publication Data
US 2019/0301988 A1    Oct. 3, 2019

(30) Foreign Application Priority Data
Nov. 23, 2016    (IN)  .............................. 201621040010

(51) Int. Cl.
*G01N 1/40*        (2006.01)
*B01D 21/26*       (2006.01)
(Continued)

(52) U.S. Cl.
CPC ......... *G01N 1/4077* (2013.01); *B01D 21/262* (2013.01); *C07K 1/14* (2013.01);
(Continued)

(58) Field of Classification Search
CPC ........ B01D 21/262; C07K 1/14; C07K 1/145; C12N 15/1003; G01N 1/38; G01N 1/4077;
(Continued)

(56) References Cited

U.S. PATENT DOCUMENTS

| | | |
|---|---|---|
| 2004/0241176 A1 | 2/2004 | Lamparski et al. |
| 2013/0273544 A1 | 10/2013 | Vlassov et al. |
| 2016/0160181 A1 | 6/2016 | Kreke et al. |

FOREIGN PATENT DOCUMENTS

| | | |
|---|---|---|
| EP | 2875348 A1 | 5/2015 |
| WO | 2016172598 | 10/2016 |

OTHER PUBLICATIONS

Zeringer E et al.: "Strategies for isolation of exosomes", Cold Spring Harbor Protocols, Apr. 1, 2015, doi:10.1101/pdb.top074476, pp. 319-323.

(Continued)

*Primary Examiner* — Jennifer Wecker
*Assistant Examiner* — Kathryn Elizabeth Limbaugh
(74) *Attorney, Agent, or Firm* — Shumaker, Loop & Kendrick, LLP

(57) ABSTRACT

Methods and kits for isolation of cell-derived vesicles and their associated macromolecules like nucleic acids, proteins, lipids metabolites etc. from one or more blood, serum, plasma, saliva, urine, cerebrospinal fluid, breast milk, tear, conditioned culture media etc. to assist detection, prevention, and understanding of disease biology. The invention offers various advantages including simple technical solutions which are cost-effective, time-saving and scalable for large industrial outputs.

27 Claims, 10 Drawing Sheets

(51) Int. Cl.
    *C07K 1/14*           (2006.01)
    *C12N 15/10*         (2006.01)
    *G01N 1/34*          (2006.01)
    *G01N 1/38*          (2006.01)
    *G01N 33/49*         (2006.01)
    *G01N 33/493*       (2006.01)
    *G01N 33/50*         (2006.01)

(52) U.S. Cl.
    CPC .......... *C07K 1/145* (2013.01); *C12N 15/1003* (2013.01); *G01N 1/34* (2013.01); *G01N 1/38* (2013.01); *G01N 33/491* (2013.01); *G01N 33/493* (2013.01); *G01N 33/50* (2013.01)

(58) Field of Classification Search
    CPC ...... G01N 1/34; G01N 33/491; G01N 33/493; G01N 33/50
    See application file for complete search history.

(56) References Cited

OTHER PUBLICATIONS

Written Opinion for PCT/IB2017/057360 dated Feb. 19, 2018 (7 pgs.).
International Search Report (ISR) for PCT/IB2017/057360 dated Feb. 19, 2018 (4 pgs.).

METHOD AND KIT FOR EXOSOMES AND ASSOCIATED BIOMACROMOLECULES CAPTURE

CROSS-REFERENCE TO RELATED APPLICATIONS AND PRIORITY

The present application claims priority from the provisional patent application filed on 23 Nov. 2016 having application number 201621040010.

TECHNICAL FIELD

The present invention relates to the fields of medicine, cell biology, molecular biology and genetics. The invention relates particularly to assays, diagnostic kits and methods for isolating cell-derived vesicles, more particularly, relates to isolation of exosomes from biological samples like cell culture media, urine, saliva, serum, blood etc. for disease detection, disease prevention and understanding disease biology.

BACKGROUND

Exosomes are cell-derived vesicles, preformed microvesicles that are released from the cell following the exocytic fusion of intracellular multi-vesicular bodies with the plasma membrane and are nano-scale vesicles secreted by cells in almost all organisms and contain biomacromolecules (DNA, RNA, Proteins, lipids, metabolites etc.). Exosomes (30-100 nanometer in size) represent a miniaturized cell (5-10 micrometer size). Exosomes originate from the intraluminal vesicles of late endosomal compartments named multi-vesicular bodies and the fusion of these late endosomes with the cell membrane result in the release of the vesicles into the extracellular compartment.

Exosomes were once thought to be "trash bags" for cells to discard unwanted proteins. However, exosomes are increasingly viewed as having important physiological function particularly in cellular communication. In recent years, exosomes derived from tumour-pulsed dendritic cells, neoplastic cells, and malignant effusions have been shown to be able to present antigens to T-cells, and has led to numerous studies employing these vesicles as biomarkers in the diagnosis of diseases like cancer, diabetes, hepatitis, Alzheimer's, Parkinson's etc.

In the present state of art, various methods are known for extraction of exosomes for further analysis of their biomacromolecular contents for disease diagnosis, drug delivery etc. Some of the known methods for exosome isolation include ultra-centrifugation, size exclusion chromatography, affinity-chromatography etc. Practically all these methods employ extended incubation times and thus these known methodologies are constrained by technical limitations and other drawbacks like being labour intensive, time-consuming, damaging the integrity of the exosomes and being costly.

In accordance with the present state of the art, what is needed are methods, processes, kits and assays for rapid and inexpensive isolation exosomes wherein such methods have little or no incubation time, utilize common laboratory reagents and apparatus, and do not require high speed centrifugation, such as ultracentrifugation and wherein the use of low speed centrifugation, that uses centrifugal forces significantly less than 10,000×g, can be used to isolate high quality exosomes.

Accordingly, the present invention, which provides new kits and methods for isolation of exosomes and associated macromolecules like nucleic acids, proteins, lipids metabolites etc. from blood, serum, plasma, saliva, urine, cerebrospinal fluid, breast milk, tear, conditioned culture media etc. to assist detection, prevention, and understanding of disease biology, is of immense significance and may solve a long-standing pressing need.

SUMMARY

This summary is provided to introduce aspects related to development of a method and kit for capture of exosomes and associated biomacromolecules. This summary is however not intended to disclose essential features of the innovation and nor is intended to determine, limit or restrict the scope of the innovation.

The present invention directs to the intent of finding quick and accurate methods for isolation of exosomes and associated macromolecules like nucleic acids, proteins, lipids, metabolites etc. from a plurality of samples like conditioned culture media from cell lines, plasma, blood, serum, saliva, urine, cerebrospinal fluid, breast milk, tear etc. to assist detection, prevention, and understanding of disease biology.

In accordance with one aspect of the present invention, the features of the methods and kits for isolation of cell-derived vesicles from a biological sample, wherein the method comprises an initial step of adding macromolecule-stabilizing compounds to the biological sample to obtain a mixture and mixing said mixture, or optionally, an initial step of adding a diluent to the biological sample to obtain a mixture and mixing said mixture followed by addition of macromolecule-stabilizing compounds and mixing said mixture comprising the biological sample, the diluent and the macromolecule-stabilizing compounds, are disclosed. The method may comprise a further step of adding a volume-excluding polymer to the mixture of step one to obtain an admixture. The method may comprise a third step of centrifugation of the admixture of step two in a table top centrifuge for a predetermined time in the range of 10 minutes to 20 minutes to obtain a pellet and a supernatant. The method may comprise a fourth step of removing the supernatant and washing the pellet a buffer solution of predetermined concentration and may finally comprise a fifth and final step of resuspending the pellet in a buffer solution of predetermined concentration to produce isolated cell-derived vesicles, characterized in that, said cell-derived vesicles comprise exosomes having yield in the range of $2.2 \times 10^{12}$ to $4.5 \times 10^{14}$.

In accordance with another aspect of the present invention, the features of the methods and kits for isolation of cell-derived vesicles from a biological sample which may comprise biological fluid including but not limited to blood serum, plasma, whole blood, urine, saliva, semen, breast milk, joint fluid, cerebrospinal fluid, sweat, tears, vaginal fluid, or amniotic fluid or alternatively may comprise cell culture media obtained from cell lines including but not limited to HEK293T, LN229, MCF7A, SiHa, Hela, C33a, Caski, A549, A431, or Jurket, are disclosed.

In accordance with another aspect of the present invention, the features of the methods and kits for isolation of cell-derived vesicles from a biological sample, wherein the diluent may be preferably phosphate buffered saline solution with a concentration 1% weight/weight and used in an amount of 40% volume by volume of the reaction mixture, are disclosed.

In accordance with another aspect of the present invention, the features of the methods and kits for isolation of cell-derived vesicles from a biological sample, wherein the volume-excluding polymer may be preferably polyethylene glycol and may have molecular weight in the range of 1000 Daltons to 5000 Daltons at a pH in the range of 7.2 to 7.6 and may be added at a concentration of 10% to 25% w/v of the sample.

In accordance with another aspect of the present invention, the features of the methods and kits for isolation of cell-derived vesicles from a biological sample, wherein the macromolecule-stabilizing compounds may comprise sodium salts of organic compounds having a general formula $C_6H_{12}O_7$ at a molar concentration in the range of 20% to 50% and may be added at an amount of 0.2% to 5% weight/volume.

In accordance with another aspect of the present invention, the features of the methods and kits for isolation of cell-derived vesicles from a biological sample, isolated cell-derived vesicles secreted from a biological sample obtained at the end of said fifth step, comprises exosome-marker proteins including but not limited to CD63 antigen (CD63), CD9 antigen (CD9), CD81 antigen (CD81), are disclosed.

In accordance with another aspect of the present invention, the features of the methods and kits for isolation of cell-derived vesicles from a biological sample, wherein the yield of protein extracted from said isolated cell-derived vesicles may be in the range of 75 microgram per millilitre to 500 microgram per millilitre of said biological sample, and wherein yield of RNA extracted from said isolated cell-derived vesicles may be in the range of 250 nanogram to 450 nanogram per one millilitre of said biological sample, and wherein the yield of DNA extracted from said isolated cell-derived vesicles may be in the range of 100 nanogram to 250 nanogram per millilitre of said biological sample, are disclosed.

In accordance with another aspect of the present invention, the features of a method for producing a cell-derived-vesicles-depleted serum, wherein the serum may be at least partially depleted of the cell-derived-vesicles, are disclosed.

In accordance with another aspect of the present invention, the features of a kit for isolation of cell-derived vesicles secreted from a biological sample, wherein said kit may comprise, a solution A, comprising a macromolecule-stabilizer compound, a solution B, comprising a volume-excluding polymer, and a solution C comprising a diluent comprising a buffered solution, characterized in that, said cell-derived vesicles comprise exosomes which may have a yield in the range of $2.2 \times 10^{12}$ to $4.5 \times 10^{14}$, are disclosed.

In still another aspect of the invention, the features of the kit for exosome and associated biomacromolecules isolation that enable use of kit in cancer diagnosis and diagnosis and detection of other diseases like hepatitis, Alzheimer's, diabetes as well as for drug delivery and drug discovery methods, are disclosed.

BRIEF DESCRIPTION OF THE DRAWINGS

The detailed description is described with reference to the accompanying figure. In the figure, the left-most digit(s) of a reference number identifies the figure in which the reference number first appears. The same numbers are used throughout the drawings to refer like features and components.

Figure 1A:
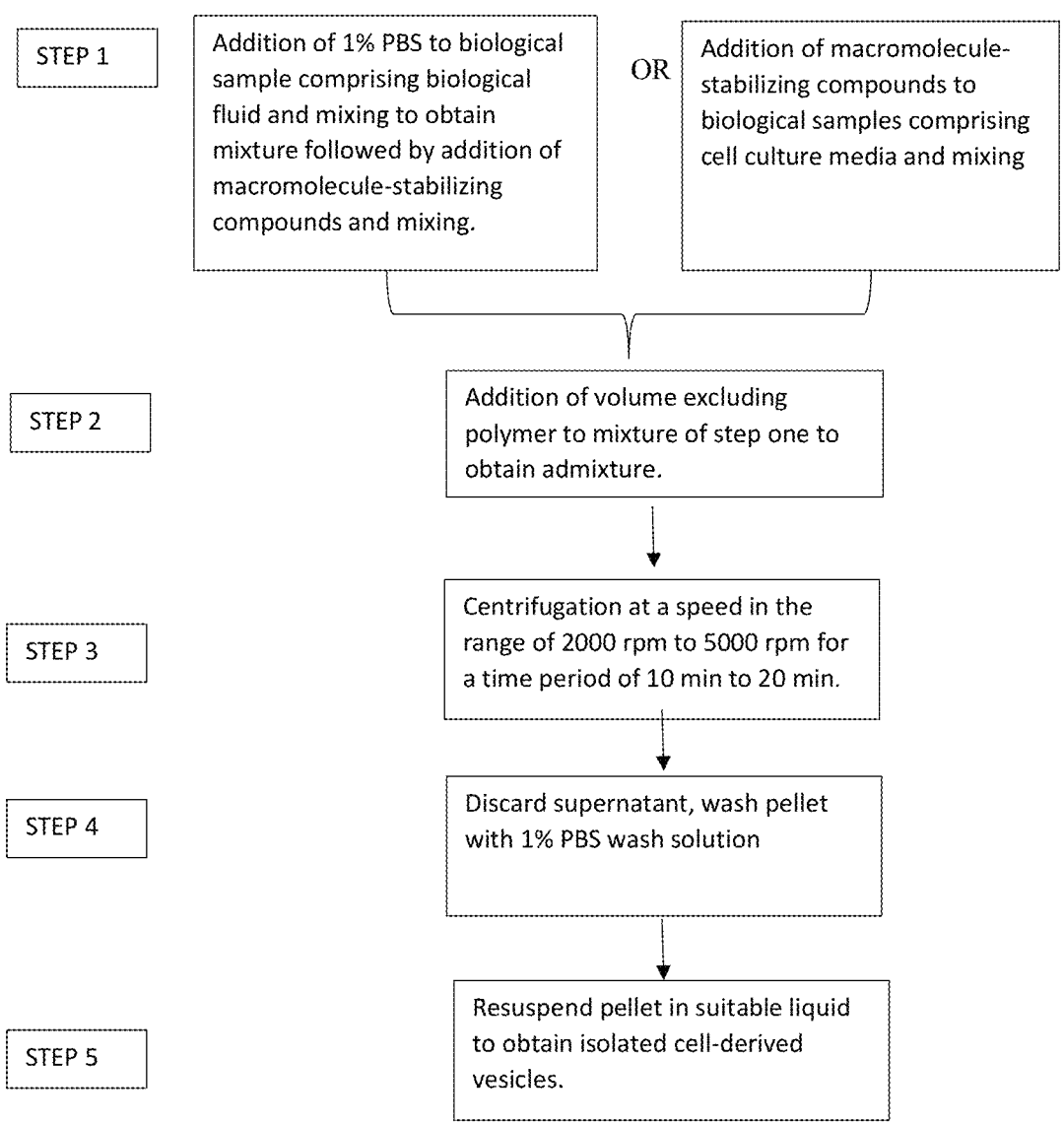
FIG. 1A illustrates the process of the invention for isolation of cell-derived vesicles from a biological sample.

The figure depicts embodiments of the present disclosure for purposes of illustration only. One skilled in the art will readily recognize from the following description that alternative embodiments of the steps illustrated herein may be employed without departing from the principles of the disclosure described herein.

DETAILED DESCRIPTION

The foregoing detailed description of embodiments is better understood when read in conjunction with the appended drawings. For the purpose of illustrating the disclosure, there are shown in the present document example constructions of the disclosure; however, the disclosure is not limited to the specific design disclosed in the document and the drawings.

The detailed description is provided with reference to the accompanying figures. In the figures, the left-most digit(s) of a reference number identifies the figure in which the reference number first appears. The same numbers are used throughout the drawings to refer like features and components.

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that, the singular forms "a," "an," and "the" include plural references unless the context clearly dictates otherwise.

The exemplary embodiments described herein and claimed hereafter may be suitably practiced in the absence of any recited feature, element or step that is, or is not, specifically disclosed herein. For instance, references in this written description to "one embodiment," "an embodiment," "an example embodiment," and the like, indicate that the embodiment described can include a particular feature, structure, or characteristic, but every embodiment may not necessarily include the particular feature, structure, or characteristic. The disclosed embodiments are merely exemplary of various forms or combinations. Moreover, such phrases are not necessarily referring to some embodiment. Further, when a particular feature, structure, or characteristic is described in connection with an embodiment, it is submitted that it is within the knowledge of one of ordinary skill in the art to affect such feature, structure, or characteristic in connection with other embodiments whether or not explicitly described.

No or terminology in this application should be construed as indicating any non-claimed element as essential or critical. The use of any and all examples, or example language (e.g., "such as") provided herein, is intended merely to better illuminate example embodiments and does not pose a limitation on the scope of the claims appended hereto unless otherwise claimed.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller subranges are also included. The upper and lower limits of these smaller ranges are also included therein, subject to any specifically excluded limit in the stated range. For example, a range of "about 0.1% to about 5%" or "about 0.1% to 5%" may be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

The present invention contains biological material i.e. biological samples comprising but not limited to blood, serum, plasma, tear, saliva, urine, conditioned cell media etc. which are commonly found throughout the territory of India as commercial products and constitute a matter of common knowledge. Therefore, all the requisite formalities related to the present application under the Biodiversity Act 2002, if any, will be undertaken for compliance before the grant of the patent.

The present invention relates to methods for isolation of cell-derived vesicles from a given biological sample and kit thereof. Broadly, several methods are used for isolation of cell-derived vesicles isolation like ultracentrifugation, precipitation and centrifugation, magnetic immuno-purification, column purification etc. and the invention discloses one such isolation method comprising precipitation and centrifugation of biological samples. The cell-derived vesicles of interest for the scope of the present invention may preferably comprise of exosomes. Exosomes are 30 nm to 100 nm vesicles and are either released from the cell when multi-vesicular bodies fuse with the plasma membrane or released directly from the plasma membrane and are deemed to play a crucial role in processes such as coagulation, intercellular signalling, and waste management. Consequently, there is a growing interest in the clinical applications of exosomes for prognosis, for therapy, and as biomarkers for health and disease and the present invention may relate to methods and processes for isolation of exosomes.

Referring now to FIG. 1, the overview of the process for isolation of cell-derived vesicles from a biological sample is represented, in accordance with an embodiment of the present invention. The invention may relate to isolation of cell-derived vesicles from a plurality of non-limiting biological samples. Some examples of the biological samples may include but are not limited to samples obtained from whole blood, blood serum, blood plasma, urine, saliva, sputum, breast milk, ascites fluid, synovial fluid, amniotic fluid, semen, cerebrospinal fluid, follicular fluid and tears. Non-limiting examples of the biological sample to be used for isolation of cell-derived vesicles may also include conditioned cell culture media, i.e., a culture media that has been used to culture cells belonging to cell lines including but not limited to cell lines like HeLa, SiHa, Me-180, C33a, Human embryonic kidney cells 293 or HEK293, human breast tumor cell line or MCF-7, LN-229 or any combination thereof.

In one exemplary embodiment of the present invention, the invention may relate to isolation of cell-derived vesicles from a biological sample, wherein the biological sample may comprise conditioned cell culture media obtained from serum enriched cell culture media. To obtain said conditioned cell culture media from said raw serum enriched cell culture, the following processing steps may be performed:
a) Seeding cells to allow favourable doublings, preferably 2.5 to 3 doublings in 10% serum (depleted of cell-derived vesicles) containing medium before harvesting of conditioned culture media. Additionally, cells may be grown at preferably 70-80% confluency in 10% serum (not depleted of cell-derived vesicles) containing medium and subsequently may be fed with 10% serum (depleted of cell-derived vesicles) containing medium for preferably another 2-3 days until they reach confluency
b) Collection of conditioned medium
c) Centrifugation at preferably 2000 rpm for preferably 5 min to remove debris
d) Transferring the centrifuged supernatant in fresh tube
e) Centrifugation of the collected supernatant at preferably 5000 rpm for preferably 20 min
f) Collection of the centrifuged supernatant in a fresh tube
g) Filtering the collected supernatant through preferably 0.22 μm filter and storing the processed supernatant at 4° C.

In another exemplary embodiment of the present invention, the invention may relate to isolation of cell-derived vesicles from a biological sample, wherein the biological sample may comprise conditioned cell culture media obtained from serum-free or low serum containing culture media. To obtain said conditioned cell culture media from said raw serum-free cell culture media, the following processing steps may be performed:
a) Seeding cells to allow preferably 2.5-3 doublings in 10% serum containing medium so as to reach preferably cell confluency at 70-80% confluency.
b) Removing culture medium and washing cell monolayer twice with 1×PBS
c) Feeding cell monolayer with either serum-free or 2% serum containing (cell-derived vesicle depleted/non-depleted serum) culture medium and allowing to grow further for preferably 2-3 days (until most preferably 100% confluency is reached)

d) Harvesting culture medium
e) Centrifugation at preferably 2000 rpm for preferably 5 min to remove debris
f) Transferring the centrifuged supernatant in fresh tube
g) Centrifugation of collected supernatant at preferably 5000 rpm for preferably 20 min
h) Collecting the centrifuged supernatant in a fresh tube
i) Filtering the collected supernatant through preferably 0.22 μm filter and storing the processed supernatant at 4° C.

Referring further to FIG. 1, the invention may relate to methods and kits for isolation of cell-derived vesicles from a biological sample, wherein, the first step of the process may comprise adding macromolecule stabilizing compound to the biological sample to obtain a mixture and mixing said mixture, in accordance with one embodiment of the present invention. The said biological sample may include a plurality of samples including but not limited to urine, saliva, sputum, breast milk, ascites fluid, synovial fluid, amniotic fluid, semen, cerebrospinal fluid, follicular fluid and tears and may also include conditioned cell culture media, i.e., a culture media that has been used to culture cells belonging to cell lines including but not limited to cell lines like HeLa, SiHa, Me-180, C33a, Human embryonic kidney cells 293 or HEK293, human breast tumor cell line or MCF-7, LN-229 or any combination thereof, however, said biological sample may not comprise blood serum or blood plasma.

In one embodiment, the invention may relate to methods and kits for isolation of cell-derived vesicles from a biological sample, wherein said biological sample may be at least 15 millilitre, may be at least 10 millilitre, may be at least 5 millilitre, may be at least 4 millilitre, may be at least 2 millilitre, may be at least 1 millilitre, may be at least 500 microliter, may be at least 200 microliter, may be at least 100 microliter or may be at least 50 microliter.

In one embodiment, the invention may relate to addition of macromolecule-stabilizing compounds to the biological sample in the first step, wherein said macromolecule-stabilizing compounds may comprise of use of kosmotrophic agents for the extraction of said cell-derived vesicles and associated biomacromolecules. The kosmotropes contribute to the stability and structure of water-water interactions by causing water molecules to favourably interact. This stabilizes intramolecular interactions in macromolecules which helps in aggregation and aid in removing impurities during the exosome extraction process.

In another embodiment of the present invention, the invention may relate to methods and kits for isolation of cell-derived vesicles from a biological sample, wherein the biological sample may comprise biological fluid including but not limited to blood serum, plasma, whole blood, urine, saliva, semen, breast milk, joint fluid, cerebrospinal fluid, sweat, tears, vaginal fluid, or amniotic fluid, and wherein, the first step of the process may comprise, an initial step of adding a diluent to the biological sample to obtain a mixture and mixing said mixture followed by addition of macromolecule-stabilizing compounds and mixing said mixture comprising the biological sample, the diluent and the macromolecule-stabilizing compounds. The said biological sample for the present embodiment may include but are not limited to, bovine serum, horse serum, human serum, rat serum, mouse serum, rabbit serum, sheep serum, goat serum, lamb serum, chicken serum and porcine serum. Such sera and plasma can also be age staged, for example, foetal bovine serum, calf bovine serum, new born calf bovine serum or adult bovine serum.

In a preferred embodiment, the invention may relate to methods and kits for isolation of cell-derived vesicles from blood serum or blood plasma from a plurality of samples, and may comprise an initial step adding a diluent to the biological sample to obtain a mixture, wherein said diluent is isotonic and helps maintain the pH and osmolality and is preferably 1% weight/weight phosphate buffered saline, followed by addition of a macromolecule-stabilizing compounds and mixing said mixture comprising the biological sample, the diluent and the macromolecule-stabilizing compounds.

In one embodiment, the invention may relate to methods and kits for isolation of cell-derived vesicles from a biological sample, wherein said kosmotrophs are metal ion binding agents to remove impurities and help obtain a highly pure, intact exosome mixture with its associated biomacromolecules.

In one embodiment, the invention may relate to methods and kits for isolation of cell-derived vesicles from a biological sample, wherein said metal ion binding agents may comprise one of the carbohydrates selected from the carbohydrates having a general formula $C_6H_{12}O_6$ or $C_6H_{22}O_{11}$.

In a preferred embodiment, the invention may relate to methods and kits for isolation of cell-derived vesicles from a biological sample, wherein said metal ion binding agents may comprise one of the carbohydrates selected from the carbohydrates having a general formula $C_6H_{12}O_6$ or $C_6H_{22}O_{11}$, wherein said carbohydrates are used at a molar concentration of 1% to 3% weight/volume.

In one embodiment, the invention may relate to methods and kits for isolation of cell-derived vesicles from a biological sample wherein the said metal ion binding agents may comprise salts of an organic compounds with the formula $C_6H_{12}O_7$ i.e. an organic compound with six-carbon chain with five hydroxyl groups terminating in a carboxylic acid group.

In an exemplary embodiment, the invention may relate to methods and kits for isolation of cell-derived vesicles from a biological sample, wherein said salts of organic compounds with the formula $C_6H_{12}O_7$ are used in the invention at a molar concentration ranging between 20% and 50% w/w of the macromolecule-stabilizing compounds and wherein said salts of organic compounds with the formula $C_6H_{12}O_7$ are used at a final concentration of 0.2% to 5% w/v of the biological sample.

In yet another embodiment, the invention may relate to methods and kits for isolation of cell-derived vesicles from a biological sample, wherein the method may comprise of use metal ion binding agents to remove impurities and help obtain a highly pure exosome mixture with its associated biomacromolecules, wherein said metal ion binding agents may comprise salts of said organic compounds and wherein the salts are preferably salts of sodium.

In one embodiment, the invention may relate to methods and kits for isolation of cell-derived vesicles from a biological sample, wherein the method may comprise of sodium salts of said organic compounds and used as metal ion binding agents to remove impurities and wherein the said salts are non-toxic and biodegradable.

In one embodiment, the invention may relate to methods and kits for isolation of cell-derived vesicles from a biological sample, wherein the method may comprise a second step of addition of a volume excluding polymer to the mixture of step one to obtain an admixture.

In another embodiment of the present invention, the invention may relate to methods and kits for isolation of cell-derived vesicles from a biological sample through the use of precipitation methods which may comprise volume excluding polymers including but not limited to use of polymerization products of ethylene oxide. The use of polymerization products of ethylene oxide for the said isolation of exosomes from a biological sample. Polyethylene glycol (PEG) is known to a person of ordinary skill in the art as a polymerized product of ethylene oxide and as an ideal precipitant for isolation of biological components like exosomes to assist detection, prevention, and understanding of disease biology. More specifically, the invention relates to the use of a low molecular weight polyethylene glycol mixture at a specific concentration without the sample having to undergo any incubation process for isolation of high-fidelity exosomes PEG precipitation is a technique known to a person of ordinary skill in the art and is a simple method that operates at ambient temperature and exhibits fast precipitation kinetics and the invention also comprises of a kit with specific low weight PEG at a specific concentration for the exosome isolation. In the existing art, various inventions relating to the use of polyethylene glycol precipitation and centrifugation methods exist for isolation of exosomes. However, most of them use a two-step centrifugation process, the first employing low speed centrifugation and the second employing a high-speed ultracentrifugation step. This increases the experimental time and also requires an additional incubation step. Thus, a commercial process, kit, method is not available to facilitate this isolation in a time-efficient manner while at the same time ensuring high purity and stability of the isolated exosomes. Also, the commercial kits available purporting to isolate exosomes and associated biopolymers suffer from various drawbacks, including but not limited to, lack of purity in the isolated samples, lack of standardization, lack of sensitivity and necessity of expensive infrastructure like ultracentrifuges, which the present invention is can resolve.

In one embodiment, the invention may relate to methods and kits for isolation of cell-derived vesicles from a biological sample employing a low molecular weight polymer mediated precipitation processes for exosome and associated biomacromolecules isolation to assist detection, prevention, and understanding of disease biology for a broad range of diseases like cancer, hepatitis, diabetes.

In an exemplary embodiment of the said invention, the said low-molecular weight polymer used for precipitation of the exosomes and associated biomacromolecules comprises of a polyethylene glycol solution that has an average molecular weight between and including 300 Daltons and 1,00,00,000 Daltons, specifically between 300 Daltons and 5000 Daltons and most preferably 1000 Daltons and 5000 Daltons.

In another exemplary embodiment, the invention may relate to methods and kits for isolation of cell-derived vesicles from a biological sample wherein the said method or kit may comprise employing a PEG with a molecular weight between 1000 Daltons and 5000 Daltons and having a specific concentration wherein the said concentration of the PEG may range from 10% PEG to 25% PEG by weight.

In one embodiment, the invention may relate to methods and kits for isolation of cell-derived vesicles from a biological sample wherein the method may comprise of use of PEG with a molecular weight between 1000 Daltons and 5000 Daltons and having a specific concentration between 10% and 25% and wherein the said PEG solution is prepared by mixing the said PEG in distilled water.

In another embodiment, the invention may relate to methods and kits for isolation of cell-derived vesicles from a biological sample wherein the method may comprise of use of PEG with a molecular weight between 1000 Daltons and 5000 Daltons and having a specific concentration between 10% and 25% and wherein the said PEG solution is prepared by mixing the said PEG in physiological saline such as standard phosphate buffered saline.

In a preferred embodiment, the invention may relate to methods and kits for isolation of cell-derived vesicles from a biological sample wherein the method may comprise of use of PEG with a molecular weight between 1000 Daltons and 5000 Daltons and having a specific concentration between 10% and 25% and wherein the said PEG solution is prepared by mixing the said PEG in physiological saline such as standard phosphate buffered saline at a neutral-alkaline pH in the range of 7.0 to 8.0 and more specifically in the range of 7.2 to 7.6.

In a preferred embodiment, the invention may relate to methods and kits for isolation of cell-derived vesicles from a biological sample like blood, serum, saliva, plasma urine, cerebrospinal fluid, breast milk, tear, conditioned cell culture medium etc. wherein the said PEG with a molecular weight between 1000 Daltons and 5000 Daltons and having a specific concentration between 10% and 25% and said sodium salts of said organic compounds at a concentration ranging between 20% and 50% w/v are mixed in a specific combination and in a specific ratio.

In one embodiment, the invention may the method which may comprise a third step of centrifugating admixture of step two in a table top centrifuge for a predetermined time in the range of 10 minutes to 20 minutes to obtain a pellet and a supernatant.

In another embodiment, the invention may relate to methods and kits for isolation of cell-derived vesicles from a biological sample wherein centrifugal force is applied to the sample and whereby more-dense components of the sample migrate away from the axis of the centrifuge relative to other less-dense components in the mixture. The force that is applied to the sample is a function of the speed of the centrifuge rotor, and the radius of the spin resulting in the required exosome precipitate (a pellet) which gathers at the bottom of the centrifuge tube.

In one embodiment, the invention may relate to methods and kits for isolation of cell-derived vesicles from a biological sample wherein the said centrifugation comprises of a low-speed centrifugation step.

In a preferred embodiment, the invention may relate to methods and kits for isolation of cell-derived vesicles from a biological sample wherein the said centrifugation step is carried in a normal table-top centrifuge device at a speed in the range of 1000 revolutions per minute and 5000 revolutions per minute and more preferably at a speed of around 3000 rpm at a cooling temperature and for a time not exceeding 20 minutes.

In one embodiment, the invention may relate to methods and kits for isolation of cell-derived vesicles from a biological sample which may include a fourth step of removing the supernatant and washing the pellet a buffer solution of predetermined concentration. The said wash solution is preferably phosphate buffer saline at a concentration of preferably 1% weight by volume.

Figure 1B:
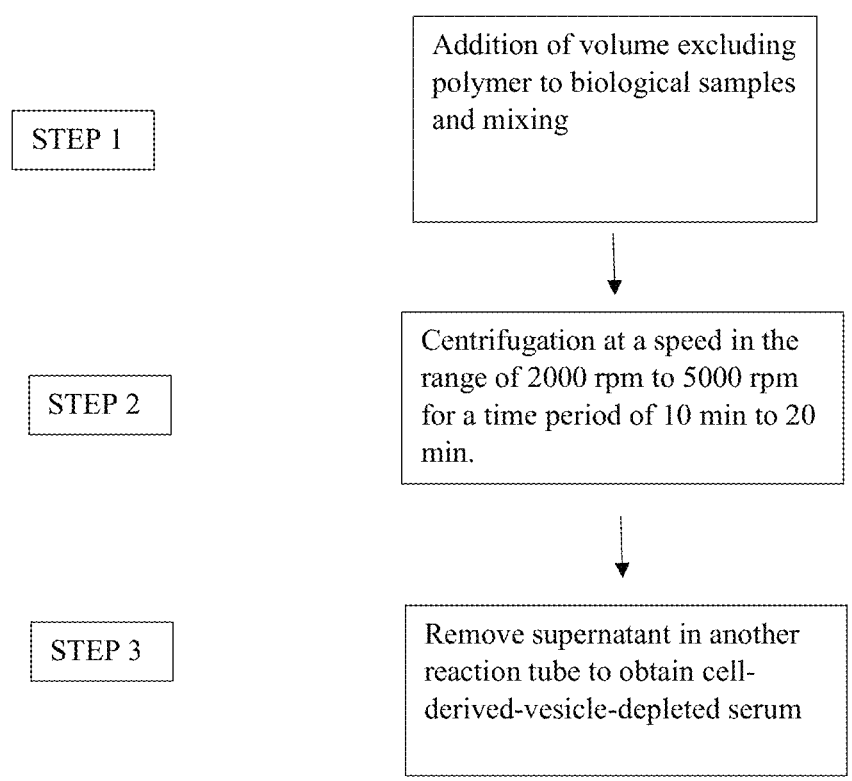
FIG. 1B illustrates the process of the invention for obtaining a cell-derived-vesicles-depleted serum.

Referring now to FIG. 1B, in another alternative embodiment, the invention may relate to methods and kits for isolation of cell-derived vesicles from a biological sample, wherein the biological sample may comprise biological serum or conditioned culture media containing serum. The said serum sample may be mixed with a volume excluding polymer comprising polymerization products of ethylene glycol with a molecular weight between 1000 Daltons and 5000 Daltons and having a specific concentration between 10% and 25% and wherein the said the solution is prepared by mixing the said volume excluding polymer in physiological saline such as standard phosphate buffered saline at a neutral-alkaline pH in the range of 7.0 to 8.0 and more specifically in the range of 7.2 to 7.6. The said mixture may be subjected to low-speed centrifugation step centrifugation step in a normal table-top centrifuge device at a speed in the range of 1000 revolutions per minute and 5000 revolutions per minute and more preferably at a speed of around 3000 rpm at a cooling temperature and for a time not exceeding 20 minutes, and the supernatant may be collected, producing said cell-derived-vesicles-depleted serum. The cell derived-vesicle-depleted serum can have a number of commercial applications. The cell-derived vesicle isolation process of the present invention yields a highly pure supernatant fraction comprising cell-derived vesicle-depleted serum containing less than $10^3$ cell-derived vesicles per ml of serum therein. The purity of the serum may be assessed by analysing the concentration of exosome marker proteins present in the supernatant exosome-depleted serum through a western blot assay.

In one embodiment, the invention may relate to methods and kits for isolation of cell-derived vesicles from a biological sample which may include a fifth and final step of resuspending the pellet in a buffer solution of predetermined concentration to produce isolated cell-derived vesicles obtained from the pellet fraction. The said buffer solution is preferably phosphate buffer saline at preferably 1% w/v.

In one embodiment, the invention may relate to methods and kits for isolation of cell-derived vesicles from a biological sample wherein said method yields a highly pure, highly stable and highly enriched pellet of exosomes containing associated biomacromolecules like nucleic acids, proteins, lipids etc. The said pellet containing the highly purified exosome formulation can be dissolved in a liquid like distilled water or a saline buffer like phosphate buffer saline to further processing.

In one embodiment, the invention may relate to methods and kits for isolation of cell-derived vesicles from a biological sample, wherein the said method provides isolated exosome fraction yields from the plurality of biological samples statistically relevant and quantifiable amount of at least 6 marker exosome-associated marker proteins including but not limited to CD9, CD63, HSP70, Flotillin1, Flotillin 2 and Alix protein. This is a crucial feature of the present invention since quantifiable amounts of a range of marker proteins offer better opportunities for therapeutic and diagnostic purposes and for drug-based targeting of the marker antigens.

In one embodiment, the invention may relate to methods and kits for isolation of cell-derived vesicles from a biological sample, wherein said method provides quantifiable yield of macromolecules like proteins, nucleic acids, lipids etc, associated with and isolated from the cell-derived vesicles. The isolation process enlisted above ensures that samples of the isolated cell-derived vesicles do not contain statistically relevant amount of cell lysate marker protein calnexin.

In one embodiment, the invention may relate to a kit for isolation of cell-derived vesicles from a biological sample, wherein said kit may comprise: a solution A, which may comprise macromolecule-stabilizer compounds, a solution B which may comprise a volume-excluding polymer, and a solution C which may comprise a diluent comprising a buffered solution, and wherein the kit may employ a method for isolation of cell-derived vesicles from a biological sample in accordance with the embodiments of the invention described in the description above.

In one embodiment, the invention may relate to methods and kits for isolation of cell-derived vesicles from a biological sample, wherein the biological sample procured is at a concentration of at least 50 microliters. Thus, the present invention confers tremendous advantages from the industrial scalability perspective. It employs very little volume and yet results in up to 10000 times increased exosome yield in the range $2.2 \times 10^{12}$ to $4.5 \times 10^{14}$ as compared to competitive products.

In another embodiment, the invention may relate to methods and kits for isolation of cell-derived vesicles from a biological sample, wherein process of isolation comprises no incubation step. The present invention is capable of providing 10000 times increased exosome yield in the range of $2.2 \times 10^{12}$ to $4.5 \times 10^{14}$ from conditioned cell culture media or other biological sample as compared to comparable competitive products, in a time period of merely 10 minutes to 20 minutes, i.e. it saves time by a factor of 36 to 72 as compared to kits requiring overnight incubation. The present invention thus confers various competitive and inventive benefits and is particularly relevant for industrial scale up of exosome isolation.

In another embodiment, the present invention provides a method or kit for exosome and associated biomacromolecules isolation in a biological sample, wherein the yield of between $2.2 \times 10^{12}$ to $4.5 \times 10^{14}$ highly pure, highly stable exosome particles per millilitre of the biofluid or culture media obtained above can be used for cancer diagnosis kits, hepatitis diagnosis kits, diabetes diagnosis kit as well as kits for drug discovery and drug delivery technologies.

Figure 2:
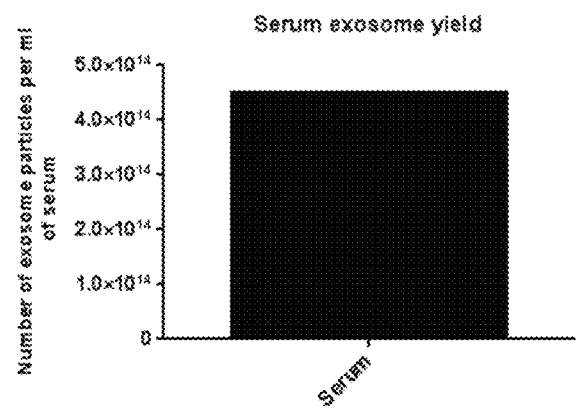
FIG. 2 illustrates yield of cell-derived vesicles isolated by the method and process illustrated in accordance with embodiments of the present invention from a biological sample comprising cell culture media.

The following examples represent non-limiting embodiments of the invention:

Example 1: Isolation of Cell-Derived Vesicles from Biological Fluids (FIG. 2)

In a reaction vessel, any biological fluid sample preferably in an amount of less than 4 millilitre, and more preferably at an amount of less than 3 millilitre but most preferably at an amount of at least 50 microliter, alternatively at least 100 microliter, alternatively at least 200 microliter, alternatively 500 microliter, alternatively at least 1 millilitre or alternatively at least 2 millilitre is introduced. To said sample is added preferably 1% weight of 40% volume by volume of a phosphate buffered saline and mixed well. Further is added preferably 1.5% w/w or alternatively 2% weight by weight or alternatively 2.5% weight by weight of a macromolecule stabilizing compound, more preferably a sodium salt of organic compounds having a general formula $C_6H_{12}O_7$ and mixed well by pipetting. To the above mixture is added a volume excluding polymer comprising preferably of a low molecular weight poly ethylene glycol and more preferably of polyethylene glycol having molecular weight not more than 5000 Daltons, but having molecular weight not less than 3000 Daltons and at least having molecular weight of 4000 Daltons in an amount of 10% weight/volume or alternatively in an amount of 12% weight by volume or alternatively in an amount of 15% weight by volume and said mixture is mixed by pipetting to obtain an admixture. The said admixture is centrifuged in a normal table top centrifuge at a cooling temperature of preferably 4 Degree Celsius for a time period of less than 20 minutes, more preferably less than 15 minutes, more preferably less than 12 minutes, more preferably less than 11 mins and more preferably at least 10 minutes, at a centrifugation speed of preferably 2000 rpm, or alternatively preferably 2500 rpm or alternatively preferably 3000 rpm. The resulting supernatant is discarded, and said pellet is washed with a 1% weight by phosphate buffered saline and said pellet is resuspended in appropriate liquid to measure the yield of exosomes per millilitre of the suspension or alternatively in terms of yield of exosome derived protein in microgram per litre. Referring to FIG. 2, the yield observed through the exemplary embodiment comprises highly pure, biocompatible exosome fraction comprising approximately $4.5 \times 10^{14}$ particles of exosome per millilitre of biological fluid i.e. an approximate increase of $10^6$ exosome yield as compared to competitive applications.

Figure 3:
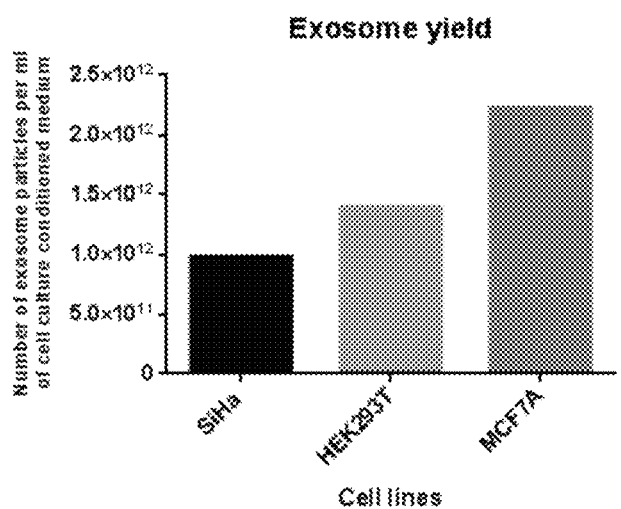
FIG. 3 illustrates yield of cell-derived vesicles isolated by the method and process illustrated in accordance with embodiments of the present invention from a biological sample comprising serum.

Example 2: Isolation of Cell-Derived Vesicles from Cell Culture Media (FIG. 3)

In a reaction vessel, any conditioned cell culture media in accordance with the embodiments of the present invention sample preferably in an amount of less than 4 millilitre, and more preferably at an amount of at least 50 microliter, alternatively at least 100 microliter, alternatively at least 200 microliter, alternatively 500 microliter, alternatively at least 1 millilitre, or alternatively at least 1 millilitre is introduced. To said sample is added preferably 1.5% w/w or alternatively 2% weight by weight or alternatively 2.5% weight by weight of a macromolecule stabilizing compound, more preferably a sodium salt of organic compounds having a general formula $C_6H_{12}O_7$ and mixed well by pipetting. To the above mixture is added a volume excluding polymer comprising preferably of a low molecular weight poly ethylene glycol and more preferably of polyethylene glycol having molecular weight not more than 5000 Daltons, but having molecular weight not less than 3000 Daltons and at least having molecular weight of 4000 Daltons in an amount of 20% weight/volume or alternatively in an amount of 22% weight by volume or alternatively in an amount of 25% weight by volume and said mixture is mixed by pipetting to obtain an admixture. The said admixture is centrifuged in a normal table top centrifuge at a cooling temperature of preferably 4 Degree Celsius for a time period of less than 25 minutes, more preferably less than 22 minutes, more preferably less than 21 minutes, preferably at least 20 mins and more preferably at least 15 minutes, at a centrifugation speed of preferably 1500 rpm, or alternatively preferably 2000 rpm, or alternatively preferably 2500 rpm or alternatively preferably 3000 rpm. The resulting supernatant is discarded, and said pellet is washed with a 1% weight by phosphate buffered saline and said pellet is resuspended in appropriate liquid to measure the yield of exosomes per millilitre of the suspension or alternatively in terms of yield of exosome derived protein in microgram per litre. Referring to figure 2,150 the yield observed through the exemplary embodiment comprises highly pure, biocompatible exosome fraction comprising approximately in the range of $1 \times 10^{12} 2.2 \times 10^{12}$ particles of exosome per millilitre of a plurality of cell culture sample i.e. an approximate increase of $10^4$ exosome yield as compared to competitive applications.

Example 3: Estimation of Exosomal Protein from Isolated Cell-Derived Vesicles (FIG. 4)

Figure 4:
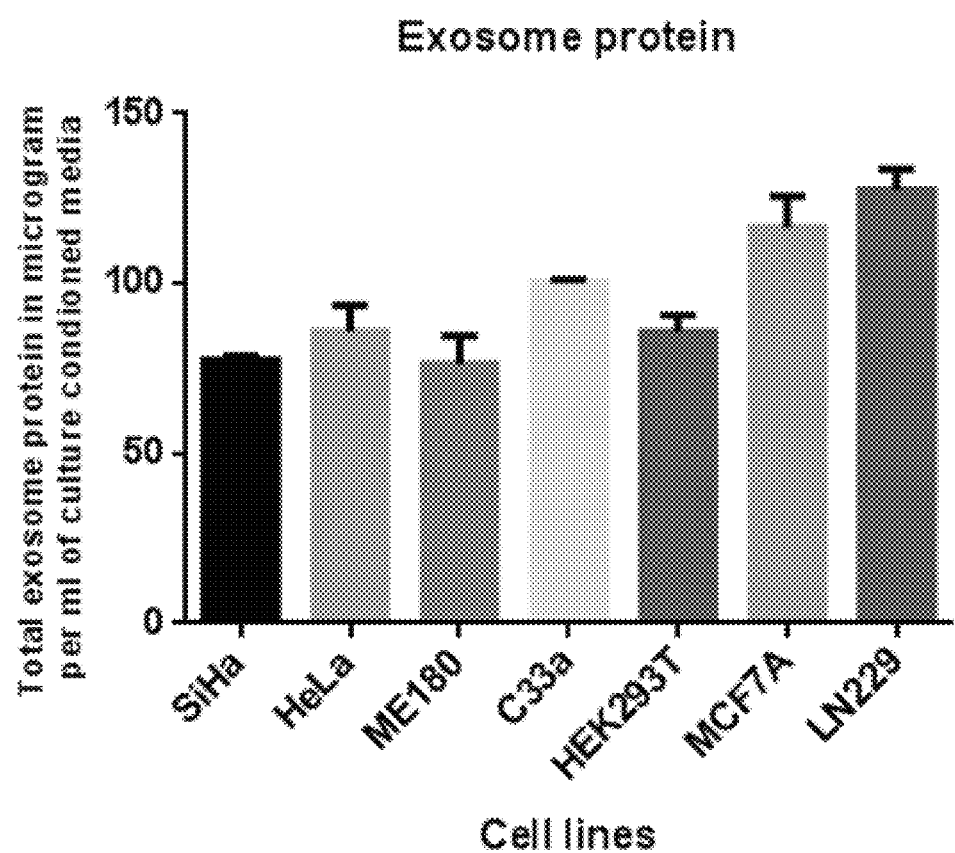
FIG. 4 illustrates yield of proteins from cell-derived vesicles isolated by the method and process illustrated with embodiments of the present invention from a plurality of biological samples

Referring now to FIG. 4, exemplary embodiments describing yield of protein through methods known in the common art from a biological sample wherein the above steps in the said proportions and by following the said sequence of events, results in a yield of exosome-derived protein in the range of 75 microgram per millilitre to 500 microgram per millilitre of said biological sample, wherein the sample comprises cell-culture media from one or more cell lines is described Example 4: Estimation of Nucleic Acids from Isolated Cell-Derived Vesicles (FIG. 5)

Figure 5A:
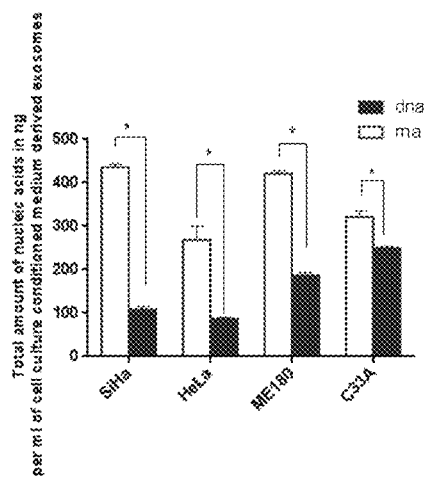
FIG. 5 illustrates yield of nucleic acids from cell-derived vesicles isolated by the method and process illustrated in accordance with embodiments of the present invention from a plurality of biological samples.

Referring now to FIG. 5A, exemplary embodiments describing yield of nucleic acids through methods known in the common art from a biological sample wherein the above steps in the said proportions and by following the said sequence of events, results in a yield of exosome-derived deoxyribose nucleic acid or DNA in the range of 100 nanogram to 250 nanogram per millilitre of said biological sample, wherein biological sample comprises cell culture media, is described.

Figure 5B:
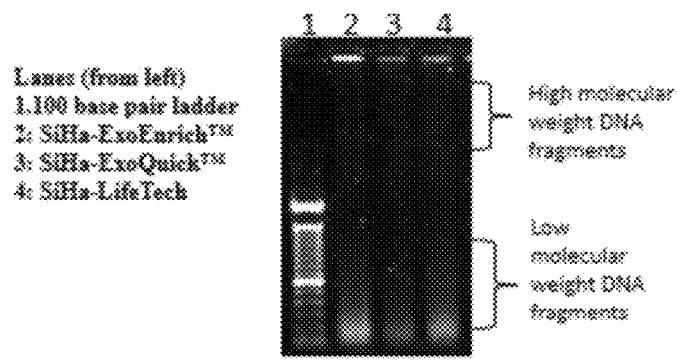

FIG. 5B represents DNA separation from cell culture media on 0.8% agarose gel. To obtain the said result: the first step comprises casting a 0.8% agarose gel with added SYBER SAFE dye to visualize DNA in gel followed by loading DNA samples and running gel for 1 hour. The results are visualized using a Chemi Doc, XRS system (BioRad laboratories, USA).

Figure 5C:
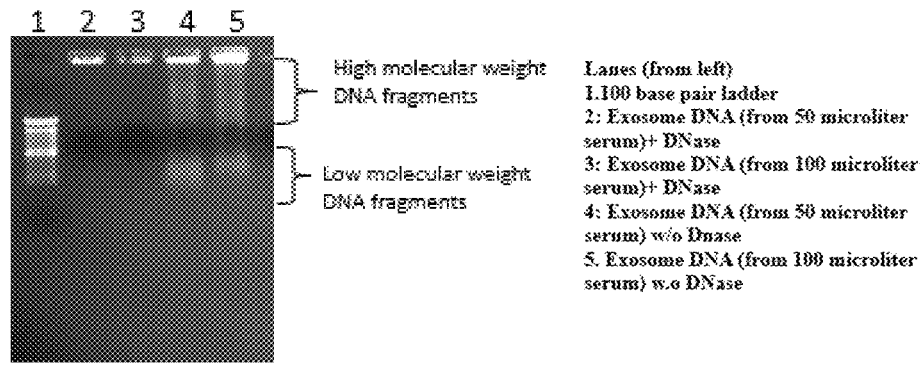

FIG. 5C represents DNA separation from serum samples on 0.8% agarose gel in presence and absence of DNA digesting enzymes as visualized using (ChemiDoc XRS, BioRad Laboratories, USA).

Further, exemplary embodiments describing yield of RNA through methods known in the common art from a biological sample wherein the above steps in the said proportions and by following the said sequence of events, results in a yield of results in a yield of exosome-derived ribose nucleic acid or RNA in the range of 250 nanogram to 450 nanogram per millilitre of said biological sample is described.

Figure 5D:
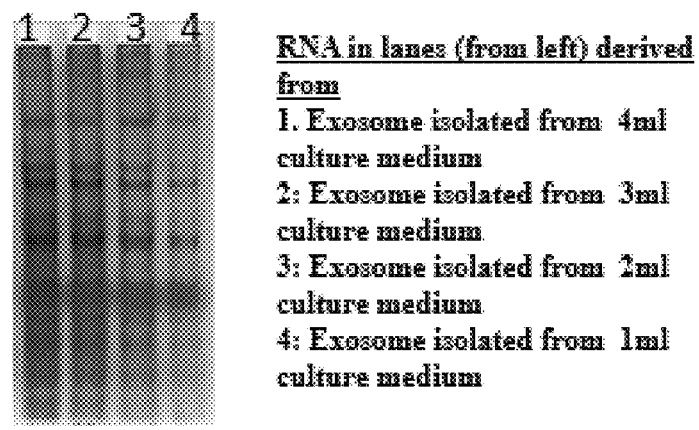

FIG. 5D represents exosome RNA separation on 15% Polyacrylamide gel wherein RNA is stained with silver staining method. To obtain said result: first step is loading RNA samples and running a PAGE gel, followed by fixing gel in 150 ml of 50% methanol+5% acetic acid for 18 minutes, washing in 150 ml 50% methanol for 10 minutes, followed by washing with dH2O, incubation with 150 ml of sodium thiosulphate for 1 minute followed by rinsing in water for 1-minute, submerging gel in 150 ml of 0.1% silver nitrate with 0.8% formalin (37%) for 18 minutes, followed by rinsing with water for 1 minute, followed by incubation with 150 ml of 2% sodium carbonate with 0.04% formalin (37%) until required intensity of color develops. The last step is washing the gel, first with in 150 ml 5% acetic acid for 10 minutes followed by washing in water for 5 minutes and visualizing gel documentation system (ChemiDoc XRS, BioRad Laboratories, USA).

Example 5: Scanning Electron Microscope Imaging of Isolated Cell-Derived Vesicles (FIG. 6)

Figure 6A:
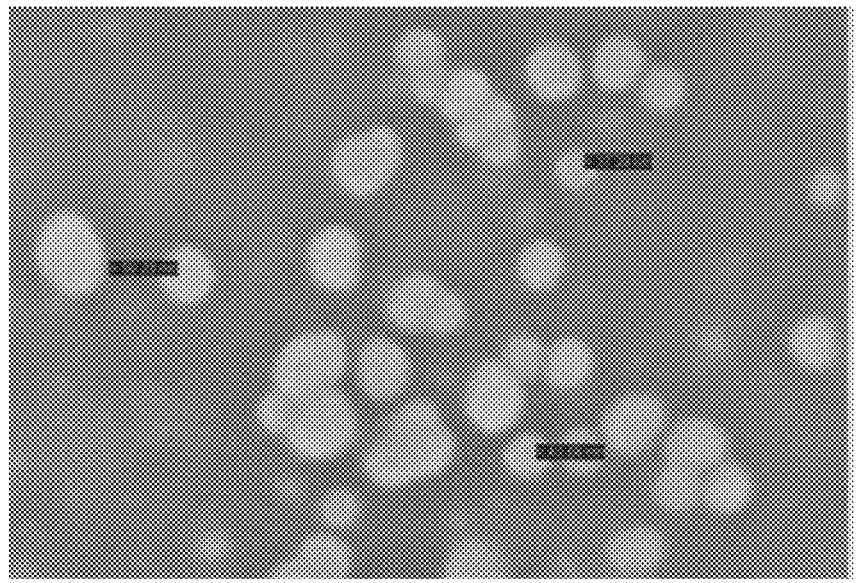
FIG. 6 illustrates scanning electron microscopy images of the isolated cell-derived vesicles in accordance with embodiments of the present invention from a plurality of biological samples.
Figure 6B:
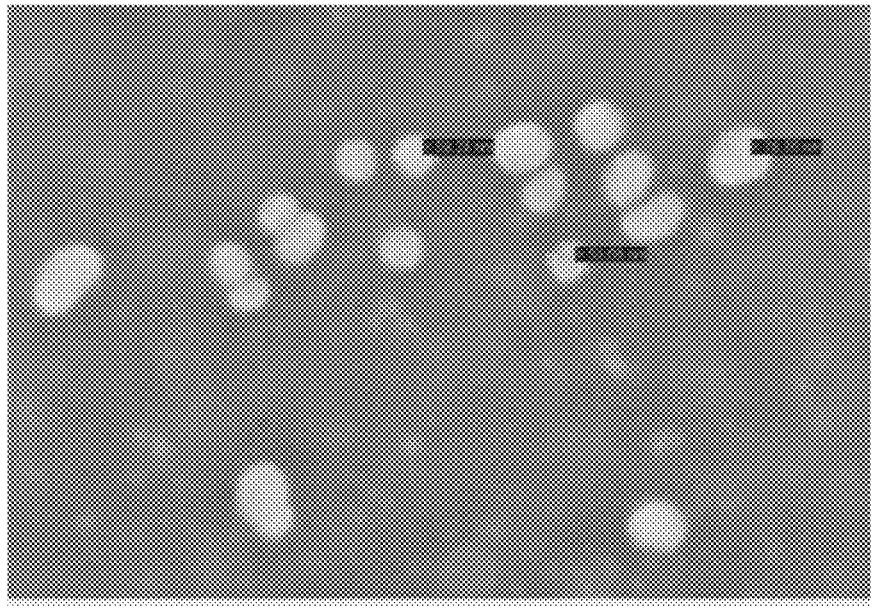

Referring now to FIG. 6, FIG. 6A represents scanning electron microscopy of cell culture conditioned medium isolated exosomes. FIG. 6B represents scanning electron microscopy of serum isolated exosomes. The images are obtained by the following procedure: isolation of exosomes from 2 ml of cell culture conditioned medium or 50 microliter of serum using PEG, followed by a step of washing the exosome pellet in 1× Phosphate buffer saline for approximately 3 minutes at 3000 rpm, followed by dissolving the exosome pellet in approximately 500 microliter of distilled water, followed by drop casting the resuspended exosomes in onto the grid, followed by gold sputtering the grid for 10 minutes using 5 nm gold and imaging in a scanning electron microscope at a 200 nm resolution scale.

Example 6: Quantification of Exosome Activity Using Acetylcholine Esterase Colorimetric Assay (FIG. 7)

Figure 7A:
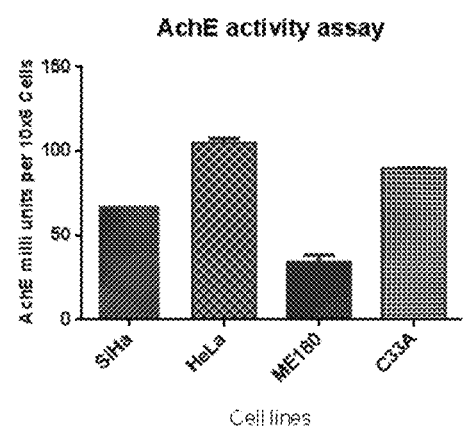
FIG. 7 illustrates acetylcholine colorimetric assay of the exosome isolated fraction in accordance with embodiments of the present invention from a plurality of biological samples.
Figure 7B:
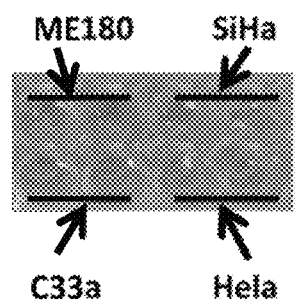

Referring now to FIG. 7, the figure represents quantification of exosome activity using acetylcholine esterase colorimetric assay. To obtain the said result: isolation of exosomes from preferably 4 ml cell culture conditioned medium, followed by resuspension of exosome pellet in 50 microliter of phosphate buffer saline, followed by adding 10 microliter of exosome suspension in a 96 well plate and adding 20 microliters of preferably 6-10 mM DTNB solution followed by 170 microliter of 0.5-1 mM acetyl choline iodide and reading absorbance or color at 405 nm using a microplate reader. The colorimetric assay gives a better understanding of the presence and activity of exosomes in the pelleted fraction, since acetylcholine esterase is a membrane bound marker and thus indicates with substantial clarity, presence of cell-derived vesicles.

Example 7: Detection of Exosome Marker Proteins and Exosome Purity Check (FIG. 8)

Figure 8:
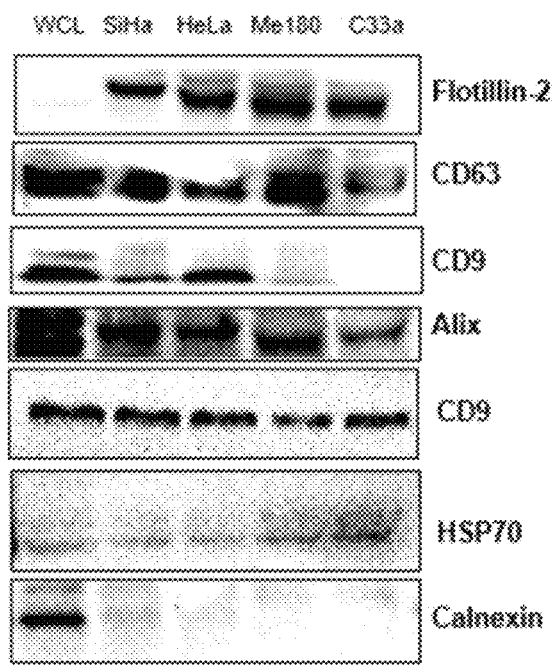
FIG. 8 illustrates western blot images of cell lysate and exosome marker proteins for understanding localization of exosomes after isolation in accordance with embodiments of the present invention from a plurality of biological samples.

Referring now to FIG. 8, the figure represents detection of exosome marker proteins and exosome purity check. To obtain the said results a Western Blot is run and exosome proteins were resolved using SDS-PAGE run and proteins were transferred onto a FluoroTrans PVDF membrane (Pall Corporations USA), followed by membrane blocking using 5% BSA in PBS buffer for 1 hours at room temperature. Further, immunoblotting was performed using primary antibodies for each of marker proteins (at 1:2000 dilution, for over-night incubation at 4 degree) and membrane was incubated with a secondary antibody (1:5000 dilution, for 1 hours at room temperature). Further, membrane was washed thrice using a 0.1% Tween-20 containing PBS buffer and signal was developed using a Optiblot ECL detection kit (abcam, UK, Cat: ab133406). The primary antibodies procured comprise: Flotillin-2—abcam, UK, Cat: (ab181988); CD63—Cloud Clone Corp, USA, Cat: (PAB345Hu01); CD9—(abcam, UK, cat: ab92726); Alix—Cloud Clone Corp, USA (PAB247Hu01); HSP70—abcam, UK (ab47455); Calnexin—Cell Signalling Technologies, USA (Cat: 2679); Secondary antibodies: Anti-Rabbit HRP (Pierce, USA) Anti-Mouse HRP (Pierce, USA). It can be clearly seen that the cell lysate marker protein calnexin is not present in statistically relevant amount in the isolated exosome fraction obtained from various cell lines while the exosome marker flotillin protein is present in all the exosome samples indicting purity of extraction.

Example 8: Biocompatibility of Isolated Exosomes (FIG. 9)

Figure 9:
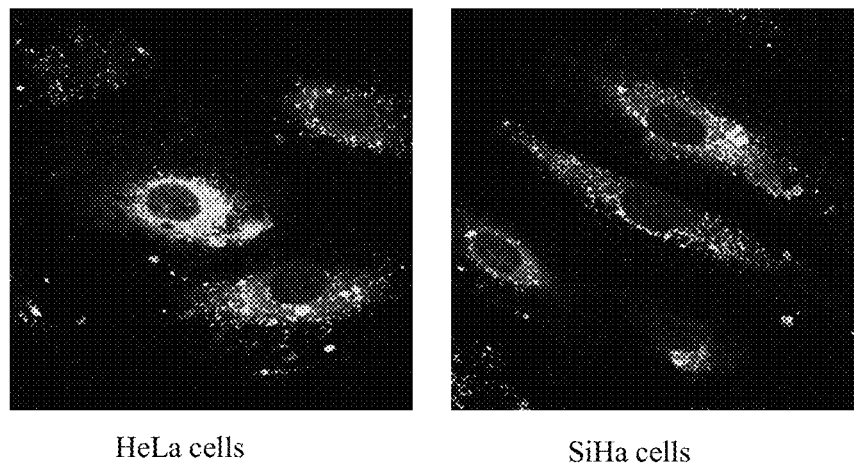
FIG. 9 illustrates western blot images of exosome marker proteins from a plurality of biological samples characterized by time period of centrifugation in accordance with embodiments of the present invention.

Referring now to FIG. 9, the figure represents biocompatibility of isolated exosomes. To obtain said result, the following steps are followed. Approximately 4 ml cell culture conditioned media of HEK23T cells (preferably grown in DMEM medium containing exosome depleted serum at preferably final concentration of 10%) was mixed with 25% sodium gluconate at final concentration PEG-4000 at a final concentration of 25% was added and mixed by inverting or pipetting. The mixture be centrifuged for 20 minutes at 3000 rpm, 4 Degree Celsius. The exosome pellet be washed and resuspended in 50 microliter of phosphate buffer saline (PBS) Exosome labelling be performed using a PKH green fluorescent cell linker kit (Sigma, USA, Cat: PKH67GL) as per manufacturer's instructions. Unbound dye be neutralized by adding 2 ml of complete DMEM medium (prepared in exosome deplete serum) 50 microgram of PKH green labelled exosomes be incubated onto cell culture monolayers of HeLa, and SiHa cells. After 4 hours cells be fixed, washed and imaged in a confocal laser scanning microscope at 63× magnification. It can be clearly seen that the isolated exosomes are taken up by cells and thus can serve as crucial for a plurality of applications like drug-designing, therapeutics and diagnostics.

In one embodiment, the invention may relate to methods and kits for isolation of cell-derived vesicles from a biological sample, wherein the process provides highly pure, biocompatible, laboratory grade yield $2.2 \times 10^{12}$ to $4.5 \times 10^{14}$ exosomes from a small amount of sample comprising at least 50 microliters and in a time period of less than 20 minutes from a plurality of samples comprising conditioned cell culture media or other biological samples. The purity of the exosome preparation is evident from the acetylcholine colorimetric assay (Refer FIG. 7) as well as the western blot of marker proteins with a clear segregation of flotillin—2 protein in the pellet fraction and that of calnexin protein in the cell lysate fraction (Refer to FIG. 8). The isolated exosomes are biocompatible and easily taken up by cells (Refer FIG. 9) as detected by PKH green fluorescent cell linker experiment and thus isolated exosomes may be extremely relevant for diagnostic, therapeutic, drug-delivery and research purposes.

The foregoing description shall be interpreted as illustrative and not in any limiting sense. A person of ordinary skill in the art would understand that certain modifications could come within the scope of this disclosure.

I claim:

1. A method for isolation of cell-derived vesicles secreted from a biological sample, said method comprising:
    an initial step of adding macromolecule-stabilizing compounds to the biological sample to obtain a mixture and mixing said mixture, or optionally, an initial step of adding a diluent to the biological sample to obtain a mixture and mixing said mixture, followed by addition of macromolecule-stabilizing compounds and mixing said mixture comprising said biological sample, said diluent and said macromolecule-stabilizing compounds,
    a second step of adding a volume excluding polymer to the mixture of step one to obtain an admixture,
    a third step of centrifugation of the admixture of step two in a table top centrifuge for a predetermined time in the range of 10 minutes to 20 minutes to obtain a pellet and a supernatant,
    a fourth step of removing the supernatant and washing the pellet with a buffer solution of predetermined concentration, and
    a fifth step of resuspending the pellet in a buffer solution of predetermined concentration to produce isolated, pelleted cell-derived vesicles, characterized in that, said pelleted cell-derived vesicles comprise exosomes having yield in a range of $2.2 \times 10^{12}$ to $4.5 \times 10^{14}$, having size in the range of 30 nm to 120 nm.

2. The method of claim 1, wherein the cell is prokaryotic or eukaryotic.

3. The method of claim 1, wherein the biological sample comprises biological fluid that includes at least one of blood serum, plasma, whole blood, urine, saliva, semen, breast milk, joint fluid, cerebrospinal fluid, sweat, tears, vaginal fluid, or amniotic fluid.

4. The method of claim 1, wherein the biological sample is one from the group of cultured cell media from cell lines including at least one of HEK293T, LN229, MCF7A, SiHa, Hela, C33a, Caski, A549, A431, or Jurket.

5. The methods of claim 1, wherein the minimum biological sample volume requirement for measurable capture of exosomes is 50 microliters.

6. The method of claim 1, wherein the diluent is phosphate buffered saline solution with a concentration 1% weight/weight and used in an amount of 40% volume by volume of the reaction mixture.

7. The method of claim 1, wherein the method does not comprise any incubation step.

8. The method of claim 1, wherein the volume excluding polymer is added at an amount in the range of 10% to 25% weight/volume.

9. The method of claim 8, wherein the volume excluding polymer is one selected from the group consisting of dextran, dextran sulphate, dextran acetate, polyethylene glycol, polyvinyl alcohol or polyvinyl acetate.

10. The method of claim 9, wherein the volume excluding polymer is polyethylene glycol having molecular weight in the range of 1000 Daltons to 5000 Daltons at a pH in the range of 7.2 to 7.6.

11. The method of claim 1, wherein the macromolecule-stabilizing compounds comprise sodium salts of organic compounds having a general formula $C_6H_{12}O_7$ at a molar concentration in the range of 20% to 50% and wherein the macromolecule-stabilizing compounds are added at an amount of in the range of 0.2% to 5% weight/volume.

12. The method of claim 1, wherein the macromolecule-stabilizing compounds comprise one of the carbohydrates selected from the carbohydrates having a general formula $C_6H_{12}O_6$ or $C_6H_{22}O_{11}$ at a molar concentration in the range of 20% to 50% and wherein the macromolecule-stabilizing compounds are added at an amount of in the range of 0.2% to 5% weight/volume.

13. The method of claim 1, wherein centrifugation is carried out at a centrifugation speed in the range of 1000 to 5000 revolutions per minute at a temperature not exceeding 4 Degree Celsius.

14. The method of claim 1, wherein the buffer used for resuspending the pellet in final fifth step is 1% weight by weight phosphate buffered saline.

15. The method of claim 1, wherein the isolated cell-derived vesicles secreted from a biological sample obtained at the end of said fifth step, comprises exosomal marker proteins including at least one of CD63 antigen (CD63), CD9 antigen (CD9), CD81 antigen (CD81), HSP70, Flotillin 1, Flotillin 2 and Alix proteins.

16. The method of claim 1, wherein samples of the isolated cell-derived vesicles do not contain statistically significant amounts of cell lysate marker protein calnexin.

17. The method of claim 1, wherein the yield of protein extracted from said isolated cell-derived vesicles is in the range of 75 microgram per millilitre to 500 microgram per millilitre of said biological sample.

18. The method of claim 1, wherein exosomes are quantified by total exosome protein estimation in microgram/ml.

19. The method of claim 1, wherein exosome purity is confirmed by estimation of an exosome-membrane bound enzyme, and wherein the membrane bound enzyme is acetylcholine esterase, and wherein exosome isolation sensitivity is in the range of 0.1-1500 milliunits of acetylcholine esterase per mL of biological fluid used.

20. The method of claim 1, wherein the yield of RNA extracted from said isolated cell-derived vesicles is in the range of 250 nanogram to 450 nanogram per one millilitre of said biological sample, and wherein the yield of DNA extracted from said isolated cell-derived vesicles is in the range of 100 nanogram to 250 nanogram per millilitre of said biological sample.

21. A method for producing a cell-derived-vesicles-depleted serum, wherein the serum is at least partially depleted of the cell-derived-vesicles, said method comprising:
an initial step of adding a volume excluding polymer to biological sample to obtain a mixture,
a second step of centrifugation of the mixture of step one in a table top centrifuge for a predetermined time in the range of 10 minutes to 20 minutes to obtain a pellet and a supernatant,
a third and final step of transferring the supernatant to a suitable container thereby producing said cell-derived-vesicles-depleted serum, wherein said pelleted cell-derived vesicles comprise exosomes having yield in a range of $2.2 \times 10^{12}$ to $4.5 \times 10^{14}$.

22. The method of claim 21, wherein the serum comprises at least one of a bovine serum, a horse serum, a human serum, a rat serum, a mouse serum, a rabbit serum, a sheep serum, a goat serum, a lamb serum, a chicken serum and a porcine serum.

23. The method of claim 21, wherein the volume excluding polymer is polyethylene glycol having molecular weight in the range of 1000 Daltons to 5000 Daltons at a pH in the range of 7.2 to 7.6 and is added in the range of 10% to 25% weight by volume.

24. A kit for isolation of cell-derived vesicles secreted from a biological sample, said cell-derived vesicles comprise exosomes having yield in the range of $2.2 \times 10^{12}$ to $4.5 \times 10^{14}$, said kit comprising:
a solution A, comprising a macromolecule-stabilizer compound,
a solution B, comprising a volume excluding polymer, and
a solution C comprising a diluent comprising a buffered solution.

25. The kit of claim 24, wherein the volume excluding polymer is polyethylene glycol having molecular weight in the range of 1000 Daltons to 5000 Daltons at a pH in the range of 7.2 to 7.6 and is added in the range of 10% to 25% weight by volume.

26. The kit of claim 24, wherein the macromolecule-stabilizer compound is preferably a sodium salt of an organic compounds having a general formula $C_6H_{12}O_7$ at a molar concentration in the range of 20% to 50% and is added in the range of 0.2% to 5% weight by volume.

27. The kit of claim 24, wherein the diluent is phosphate buffered saline solution with a concentration 1% weight/weight and used in an amount in of 40% volume by volume of the reaction mixture characterized in that said biological sample is either blood serum or plasma.

* * * * *